United States Patent [19]

Hoenke et al.

[11] Patent Number: 5,132,035

[45] Date of Patent: * Jul. 21, 1992

[54] DEICING COMPOSITIONS COMPRISING CALCIUM MAGNESIUM ACETATE AND CHELATING AGENT

[75] Inventors: Karl A. Hoenke, Martinez; Jay D. Rynbrandt, San Rafael, both of Calif.

[73] Assignee: General Atomics International Services Corporation, San Diego, Calif.

[*] Notice: The portion of the term of this patent subsequent to Aug. 8, 2005 has been disclaimed.

[21] Appl. No.: 653,749

[22] Filed: Feb. 8, 1991

[51] Int. Cl.$^5$ .............................. C09K 3/18
[52] U.S. Cl. .......................... 252/70; 106/13
[58] Field of Search .............. 252/70; 106/13; 562/607, 608

[56] References Cited

U.S. PATENT DOCUMENTS

| | | | |
|---|---|---|---|
| 4,148,938 | 4/1979 | Hansen | 106/13 |
| 4,588,512 | 5/1986 | Rippie | 252/70 |
| 4,699,725 | 10/1987 | Gancy | 252/70 |
| 4,913,831 | 4/1990 | Todd, Jr. et al. | 252/70 |

FOREIGN PATENT DOCUMENTS 8805457 7/1988 World Int. Prop. O. .

Primary Examiner—A. Lionel Clingman
Assistant Examiner—Christine A. Skane
Attorney, Agent, or Firm—Heller, Ehrman, White & McAuliffe

[57] ABSTRACT

Compositions which comprises a major amount of an alkaline earth or alkali metal carboxylate, a minor amount of unreacted base and impurities, and an effective anti-staining amount of an organic chelating agent are useful as non-staining deicing compositions for use on airport runways and taxiways. The preferred alkaline earth carboxylate is calcium magnesium acetate and the preferred chelating agent is EDTA. Processes for preparation of such compositions are described.

13 Claims, 2 Drawing Sheets

DEICING COMPOSITIONS COMPRISING CALCIUM MAGNESIUM ACETATE AND CHELATING AGENT

CROSS-REFERENCE TO RELATED APPLICATIONS

The subject matter of this application is related to U.S. Ser. Nos. 144,848, and 144,359, both filed Jan. 14, 19888, U.S. Ser. No. 77,148 filed Jul. 24, 1987 and U.S. Ser. No. 003,097 filed Jan. 14, 1987.

BACKGROUND OF THE INVENTION

Removal and/or melting of snow and ice on airport runways is a major task. Moreover, because of the special corrosion problems caused by use of aluminum, aluminum alloys and other special metals on aircraft, conventional deicing compositions used on roadways, such as road salt and calcium chloride are not acceptable. Unacceptable levels of corrosion to these metals, especially to aluminum, could affect the functioning of the mechanical components as well as the structural integrity of the aircraft.

Accordingly, there have been heretofore two primary substances used to deice airport runways, one being a liquid, ethylene glycol, and the other being a solid, urea. Urea is the only solid currently acceptable for use on airport runways. The SAE standards of corrosion applying to airport deicing compositions apply only to liquids (AMS 1426A) or to urea (AMS 1730A). The differences between these two standards are due to the nature of the respective materials, but the corrosion tests are the same in both cases. However, both ethylene glycol and urea have recently been subject to criticism because of their adverse environmental effects. For example, urea may contaminate lakes and streams and is detrimental to fish and other aquatic life.

Therefore, alternative substances for use on airport runways are needed. One potential class of compounds comprises calcium magnesium acetate (abbreviated as CMA) which is made in various forms. For example, the Federal Highway Administration report entitled "Alternative Highway Deicing Chemicals" published March 1980, identified CMA as a leading candidate for replacing road salt. However, CMA fails certain corrosion tests, particularly on aluminum and aluminum alloys, by staining or discoloring the metal surface. Since there is currently no accepted SAE test procedure for measuring corrosion of solids (other than urea) for use on airport runways, we assume that AMS 1730 applies, and one of the tests under that standard is the sandwich corrosion test, test method ASTM F1110-88. We have found that commercially available CMA fails the Sandwich corrosion test by staining or discoloring test coupons.

Therefore, in that the currently acceptable deicing compositions used on airport runways are under severe criticism for their environmental disadvantages and being that conventional solid deicing compositions utilized for roads have unacceptable corrosivity for aluminum and aluminum alloys, there is a need to develop an alternative deicing composition specifically for use on airport runways.

It is therefore an object of the present invention to provide novel deicing compositions which are useful for use on airport runways and which pass the sandwich corrosion test.

It is a further object of the present invention to present methods for preparing such deicing compositions.

It is yet another object of the invention to provide calcium magnesium acetate modified by an organic chelating agent which is a useful deicing composition, while also being non-staining and non-corrosive to aluminum and aluminum alloys.

These and other objects of the invention will be apparent from the following description and from the practice of the invention.

SUMMARY OF THE INVENTION

The present invention is directed to compositions comprising a major amount of alkaline earth and/or alkali metal carboxylate, minor amounts of their precursors and/or impurities, and an effective anti-staining amount of an organic chelating agent. The preferred alkaline earth carboxylate is calcium magnesium acetate (CMA). The preferred alkali metal carboxylate is sodium formate. These compositions are useful as non-staining deicing compositions. Processes for preparing such deicing compositions are also provided. By major amount it is meant that 50% or more by weight of the dry solids comprise the composition. A minor amount is less than 50% by weight of the dry solids.

The compositions of the present invention may be prepared from readily available CMA preparations known in the art, and in particular from commercial preparations of CMA. Alternatively, the compositions of the present invention may be made by modifying processes of making CMA so that the end product CMA contains the organic chelating agent.

Methods of making CMA are known as, for example, shown in U.S. Pat. No. 4,588,512 to Rippie and U.S. Pat. No. 4,699,725 to Gancy. Particularly preferred processes for making CMA deicing compositions are disclosed in copending, commonly assigned U.S. Ser. No. 144,848, filed Jan. 14, 1988.

It is believed that one or more impurities or unreacted raw materials which are commonly contained in calcium magnesium acetate preparations which result from its processing are primarily responsible for the staining which renders CMA, as a bulk product, unacceptable as an airport deicing composition. The common impurities or unreacted raw materials found in CMA compositions are calcium or magnesium oxides or hydroxides, plus trace mineral oxides of iron, aluminum, etc. Most of these usually result from the lime used as a source of calcium for CMA.

The CMA which will comprise the major portion of the compositions according to the present invention may be any CMA preparation containing common impurities. In particular, CMA will be of the general formula $$Ca_xMg_y(CH_3COO)_{2(x+y)}$$

wherein x is about 2 to 6 and y is about 8 to 4.

The compositions according to the present invention will also contain an effective anti-staining amount of an organic chelating agent. To determine the effective anti-staining amount to be utilized with a particular CMA preparation, it will be sufficient to measure, prior to applying the organic chelating agent to the composition, the amount of unreacted base in the composition, usually present in the form of calcium oxide and/or magnesium oxide or hydroxides. The amounts of calcium acetate and magnesium acetate are usually not relevant in determining how much organic chelating agent should be added. There are also present certain other impurities, usually of unknown or at least unidentified character, some of which may be nonbasic, which will usually be present in small enough amounts so that their staining effect, if any, will be alleviated by the amount of organic chelating agent added, as determined from the unreacted base. In most preparations, particularly in commercial preparations of CMA, there is very little calcium base present and the majority of the unreacted base present will comprise magnesium base (oxide or hydroxide). Methods of measuring unreacted base, and in particular unreacted magnesium oxide, in a CMA composition are known, such as by treatment with excess acid, then back titration with base. Even if the titration indicates no presence of unreacted base in the CMA, it is advantageous to add about 0.5% by weight of the organic chelating agent to alleviate any staining which might be caused by traces of nonbasic impurities mentioned above.

In a particularly preferred embodiment, if the CMA is made in accordance with the above-referenced copending application, it will comprise less than about 3% by weight magnesium and/or calcium base and less than about 5% weight water (preferably being anhydrous). To such a composition it is preferred that a sufficient amount of chelating agent be applied so that the organic chelating agent will comprise about 3% by weight of the total composition. While not intending to be bound by a particular theory, it is believed that this amount of organic chelating agent will neutralize the staining effect of the magnesium oxide and also leave sufficient excess of chelating agent to neutralize the staining effect, if any, of trace amounts of unidentified impurities usually found in the CMA preparation.

Particularly preferred CMA which comprises the major portion of a composition according to the present invention are those of the above formula wherein x is from about 3 to 4 and where y is from about 7 to 6. Accordingly, the calcium:magnesium ratios may range from about 4:6 to about 3:7, and preferably from about 3:6 to 3:7. The preferred compositions according to the present invention will be substantially anhydrous, meaning comprising less than about 5% by water, and preferably those compositions wherein substantially all of the water molecules of hydration have been removed. By being essentially anhydrous, when the deicing composition comes in contact with ice or snow, there is a high heat of reaction due to the heat of hydration and the heat of solution, thereby improving its melting effectiveness.

According to a preferred embodiment of the present invention, compositions of a CMA and organic chelating agent are provided which comprise substantially isodimensional pellets which have bulk densities of at least 40 pounds per cubic foot particle specific gravities greater than 1.2, and attrition of less than about 3% (as measured by ASTM D 4058-81). Other superior handling characteristics of these compositions include having a fairly even size distribution, and being low in dust and low in acetic acid odor. Thus, the deicing compositions of the present invention may be distributed using conventional machinery for distributing deicing chemicals such as urea. Moreover, due to this relatively large particle size and high specific gravity, these deicing compositions are not prone to blowing away once applied to snow or ice, unlike previously used compositions comprising CMA. (See "High Sierra Is Site For CalTrans CMA Tests," *Roads & Bridges*, June 1987, pp. 48-49.)

The organic chelating agents which will be utilized to prepare the compositions of the present invention include, but are not limited to, polyphosphates, aminocarboxylicacids, 1,3-diketones, hydroxycarboxylic acids, polyamines, amino alcohols, aromatic heterocyclic bases, phenols, aminophenols, oximes, Schiff bases, tetrapyrroles, sulfur compounds, synthetic macrocycles, polymeric chelates and phosphonic acids. Typical chelating agents which may be utilized are listed, for example, in texts such as Kirk-Othmer, *Encyclopedia of Chemical Technology*, Vol. 5 (3rd Edition), pp. 343-345, John Wiley & Sons, New York, 1979, which is incorporated herein by reference.

Preferred chelating agents are the aminocarboxylic acids containing 2 to 4 carboxylic acid groups, and most preferably 3 to 4 carboxylic acid groups. The most preferred chelating agents are ethylenediaminetetraacetic acid (EDTA), hydroxyethylethylenediaminetriacetic acid (HEDTA), nitrilotriacetic acid (NTA), N-dihydroxyethylglycine (2-HxG), and ethylenebis(hydroxyphenylglycine) (EHPG). The most preferred chelating agent is EDTA, preferably in its partially neutralized form as a calcium salt. Since the preferred method of applying the chelating agent to the CMA pellets is by an aqueous solution, the chelating agent should be at least partially soluble in water. It is preferred that the organic chelating agent, in neutralized form, therefore have a solubility of at least about 0.3% by weight in water.

The deicing compositions according to the present invention are preferably prepared having a size as small as 48 Tyler mesh (about 0.295 mm diameter). Preferred particle size ranges from $-5$ to $+28$, due, in part, to the ease of use with conventional machinery for the distribution of deicing compositions.

Product size may be controlled by selecting an appropriate mesh size product screen. For example, a 7-mesh product (fines) screen may be used to meet a specification of 90% $+8$ mesh; a $7\frac{1}{2}$-mesh screen may be used to meet a specification of 90% minimum $+9$ mesh.

DEFINITIONS

As used herein, the following terms have the following meanings, unless expressly stated to the contrary.

The term "slurry" indicates a solution of a soluble substance possibly above the saturation point for the soluble substance, whether or not the solution contains non-soluble suspended material. (See, e.g., U.S Pat. No. 3,333,297.) For example, an AEC slurry may comprise an AEC solution or a solution comprising both dissolved, undissolved AEC, and unreacted raw materials.

The term "alkaline earth" refers to elements in Group IIa of the Periodic Table, and includes, for example, calcium, magnesium, barium, and the like.

The term "alkali metal" refers to metallic elements in Group Ia of the Periodic Table and includes, for example, lithium, sodium, potassium, rubidium, cesium, francium, and the like.

The term "AE base" refers to alkaline earth or alkali metal bases or mixtures thereof which are capable of reacting with a carboxylic acid to form a carboxylate salt. Typical AE bases include oxides, hydroxides, carbonates and the like of the alkaline earth and alkali metal elements. Such AE bases may contain one or more of the individual alkaline earth or alkali metal elements in various combinations and molar ratios.

The term "calcium and magnesium base" or "CM base" refers to AE bases wherein said alkaline earth or alkali metal portion comprises calcium, magnesium or mixtures thereof.

The term "magnesium base" refers to AE bases where said alkaline earth or alkali metal portion comprises magnesium.

The term "AEC" refers to alkaline earth or alkali metal carboxylates or mixtures thereof where the carboxylate group has from 1 to 4 carbon atoms. The term AEC includes single salts such as calcium acetate, magnesium acetate, and potassium acetate as well as mixed salts such as calcium magnesium acetate as well as physical mixtures or products of co-crystallization of single and/or mixed salts.

The term "CA" or "calcium acetate" refers to both anhydrous calcium acetate and its hydrates.

The term "MA" or "magnesium acetate" refers to both anhydrous magnesium acetate and its hydrates.

The term "calcium magnesium acetate" or "CMA" refers to calcium magnesium acetate (including salts wherein both calcium and magnesium are co-crystallized together as a double salt or wherein the salt is a physical mixture of calcium acetate and magnesium acetate), having the following empirical formula: $Ca_xMg_y(CH_3COO)_{2(x+y)}$, where x=about 2 to 6 and y=about 8 to 4.

The terms "calcium magnesium ratio" or "calcium to magnesium ratio" refer to the ratios of moles calcium to moles magnesium.

Unless stated otherwise, all percents refer to percent by weight.

The term "traction aid" refers to materials which help improve traction when applied to a slippery surface. Thus, the term includes inert supports which have good anti-slip properties and includes materials such as sand, crushed limestone, pulverized corncobs, nutshells (such as walnut shells, pecan shells, almond shells or the like), expanded shale, vermiculite, pumice, cinders, other substantially insoluble minerals with good anti-slip properties, or the like.

The term "mesh" refers to mesh sizes determined according to the Tyler standard sieve series.

The term "slurry pH" refers to the pH of a CMA slurry as measured by diluting one part slurry to four parts water. Preferably, the pH of a slurry will be measured of a slurry containing approximately 10% by (dry) weight solids.

DETAILED DESCRIPTION OF THE INVENTION

Figure 1:
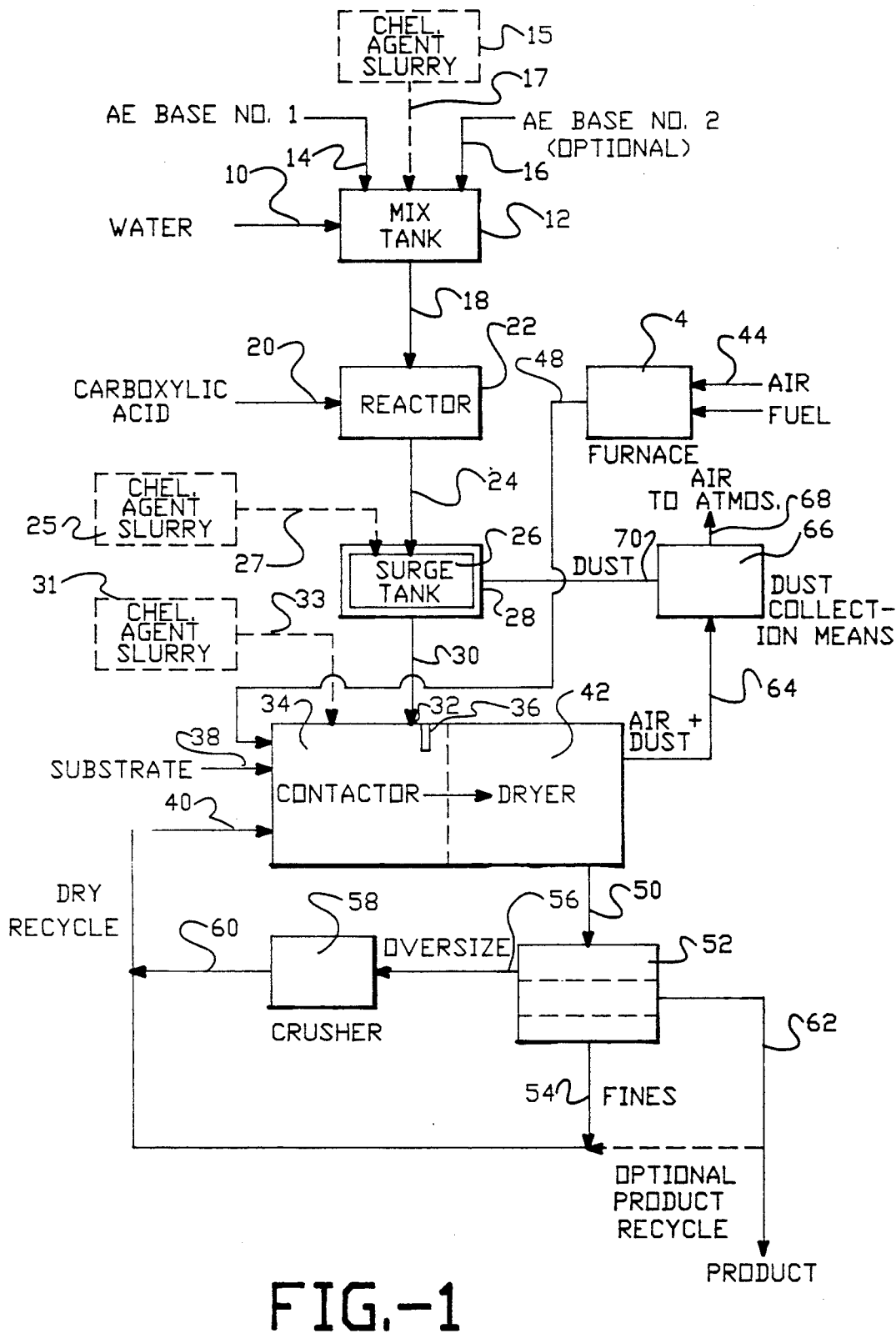
FIG. 1 is a schematic drawing showing the steps and apparatus for three processes for making compositions of the present invention.

The deicing compositions according to the present invention may be made by applying to an alkaline earth and/or alkali metal carboxylate preparation, an effective anti-staining amount of an organic chelating agent, then preferably drying to an anhydrous or substantially anhydrous form. The preferred alkaline earth carboxylate is CMA and the preferred alkali metal carboxylate is sodium formate. While it is contemplated that the compositions according to the present invention may be made without drying to a substantially anhydrous form, i.e. used in a wet or slurry form, it will be appreciated that the deicing properties would be substantially reduced when used in a wet form because of the loss of the advantage of both the heat of hydration and the heat of solution of the CMA. Exemplary CMA materials which may be formed into compositions according to the present invention are those shown for example in U.S. Pat. No. 4,588,512 to Rippie, U.S. Pat. No. 4,699,725 to Gancy and in copending, commonly assigned U.S. Ser. No. 144,848, filed Jan. 14, 1988.

To determine the amount of organic chelating agent to be applied, the CMA composition to which the chelating agent to be applied will first be analyzed for the amount present of unreacted base, typically present in the form of magnesium oxide and/or a minor amount of calcium oxide. Then an appropriate amount of organic chelating agent will be applied to the CMA in sufficient amount to at least chelate the equivalents of base present in the composition. The amount of chelating agent utilized will depend upon the chelating sites on the chelating agent molecule. Thus if EDTA is the organic chelating agent, each mole of EDTA will normally chelate two moles of magnesium ions (derived from the magnesium oxide). The preferred ratio of equivalents of chelating agent to unreacted base is in the range 0.1-100, and particularly in the range 0.5-10. The most preferred ratio is in the range 1-5.

The organic chelating agent may be applied to the CMA composition in any convenient manner such as by spraying a solution of the organic chelating agent onto particles or pellets of the CMA; or by rolling or mixing the CMA pellets in a slurry or solution of the organic chelating agent.

After the application of the organic chelating agent the composition will be dried preferably to a substantially anhydrous (usually less than about 5% by weight water) or anhydrous state. The final amount of organic chelating agent to be utilized is to be based on the dried composition.

Typically the organic chelating agent will be applied to the CMA preparation in liquid form, typically in an aqueous solution. In some instances the organic chelating agent will be insoluble or substantially insoluble in water in one of its forms. In such an instance the organic chelating agent may then be converted to a soluble form to be applied to the CMA. In this respect, it is desirable that the organic chelating agent, in its neutralized form, have a solubility in water of at least about 0.3 weight percent. Then it may be applied in solution or slurry form to the CMA and the dissolved chelating agent may penetrate into the CMA particles.

Preparation by mixing dry CMA pellets with dry powdered organic chelating agent, while still potentially useful as a deicing, non-staining composition, is not preferred and is impractical due to the difficulty of controlling the powder during transportation, storage and use. Furthermore, an outer layer of the solid organic chelating agent could form a protective coating over the CMA core, which is where the deicing properties are concentrated.

Alternatively and preferably, the compositions according to the present invention are made continuously and on-line while preparing the CMA from its precursor materials. It is most preferred therefore that the compositions according to the present invention be made by incorporating steps for addition of the organic chelating agent into the process for making CMA as disclosed in our copending Ser. No. 144,848, filed Jan. 14, 1988, which is incorporated by reference herein in its entirety.

Therefore, according to the preferred embodiment of preparing compositions according to the present invention, the organic chelating agent may be added or applied at any one of several stages during the process of making the CMA from its precursor materials. Preferably the organic chelating agent will be EDTA in a slurry containing sufficient magnesium oxide and lime to neutralize 50% of the equivalent acid groups in the EDTA. Typically this slurry will have a pH of around 8.

Preferably CM base and water are mixed in a first vessel to give a flowable aqueous CM base mixture, typically comprising at least about 40% by weight water. In one embodiment of this process the organic chelating agent (preferably partially neutralized EDTA in an MgO-lime slurry) is added to this mixture. Then the mixture is transferred to a second vessel and acetic acid is added. The CM base is reacted with a sufficient stoichiometric amount of acetic acid to give a CMA slurry having a pH which provides complete reaction of CM base and minimal acid vapor loss and also results in a CMA composition with low corrosivity. Preferably, the ratio of acetic acid to CM base is carefully adjusted to give substantially complete reaction of CM base and to minimize volatilization of unreacted acid during the subsequent distributing and drying steps. Usually, there will be less than about 3% by weight unreacted base, which remains as an impurity. Accordingly, preferably sufficient acetic acid is added to react with the CM base to give a CMA slurry with a pH of about 7 to about 9.5, more preferably from about 7.5 to 8.0, which is substantially free of acid odor. After the acetic acid addition and reaction is complete, according to a second embodiment of this process (if the organic chelating agent has not already been added) the organic chelating agent is added. Optionally, reslurried CMA dust collected by dust collection means (during the distributing and drying step) may be added to the slurry. Such addition may increase the slurry pH above 8.5, without the undesirable increase in insolubles otherwise usually seen at pH's above about 8.5. Such slurries result in a finished CMA product having a pH of about 9 to about 10 (when diluted 1 part product to 9 parts water).

Slurries having low pH's (about 5 to 6) may result in increased production of oversized product during the distributing and drying steps and in unacceptably high acetic acid emissions from an environmental standpoint.

Sufficient water is added, either alone or as part of the acetic acid solution, to give a fluid, pumpable slurry which does not solidify during processing. Preferably the slurry should contain at least about 50% by weight water to avoid excessive thickening of the slurry which can occur if the slurry drops below a temperature of about 150° F. As lower slurry moistures are employed, the resulting slurry must be heated to a higher temperature. Accordingly, preferred are slurries having at least about 50% water. Particularly preferred are CMA slurries having from about 55% to about 68% water. Slurries having lower than 55% water may also be used. Although CMA slurries having greater amounts of water may be used, such additional water later must be removed in the drying step and thus slurries having higher water contents may be less economical and disadvantageous due to increased drying costs.

Suitable CM bases include oxides, hydroxides, carbonates and the like of calcium, magnesium or mixtures thereof in various molar ratios.

Preferred CM bases include dolomitic lime, hydrated dolomitic line, preferably Type S hydrated dolomitic lime and magnesium oxide.

Preferred CM bases are those which are low in those impurities, such as iron and aluminum, which remain insoluble.

Suitable forms of acetic acid include both dilute acetic acid solutions (conventionally available as low as about 5%) and concentrated acetic acid such as glacial acetic acid and acetic acid solutions having intermediate concentrations. The acetic acid used herein may be produced by chemical or by alternative methods such as fermentation of carbonaceous materials by microorganisms and the like. Acetic acids produced by alternative methods such as microbial fermentation may have cost advantages over more concentrated acetic acid produced by conventional methods used in the chemical industry which might outweigh the economic disadvantages of possible increased drying costs due to their diluteness and thus the need to evaporate more water to obtain a dry product.

Preferred acetic acids include glacial acetic acid.

The CMA slurry is aged to allow complete reaction of CM base with acetic acid. Even when using reactive CM bases which have relative short reaction times with acetic acid, it is preferred to age the slurry. This may be done by allowing it to flow through a reactor train of several vessels before reaching the drying and pelletizing step. Reactor trains having residence times of about 3.5 to 4 hours provide sufficient time to allow complete reaction of CM base and acetic acid. Reactor trains having longer residence times, on the order of about 10 to about 13 hours, or more, may be used if desired.

Preferably, the fluid, pumpable CMA slurry is heated to a temperature of about 100° F. to about 250° F., preferably to at least about 150° F., more preferably from about 170° F. to about 200° F. Heating the CMA slurry to a relatively high temperature, preferably from about 170° F. to about 200° F. improves efficiency in the subsequent distributing step and thus yield. In addition, when slurries are not heated to a sufficiently high temperature, for example, less than about 100° F., in the distributing step much of the slurry may go to dust rather than to forming a thin layer on substrate particles. Such dust must be collected in a high efficiency dust collector such as a baghouse or wet scrubber and then is generally recycled, generally with additional water. Thus, the overall amount of water which must be removed in the drying step increases which increases manufacturing costs.

Moreover, another beneficial effect of operation with high slurry temperature is that the hardness of the CMA coating increases by 50% for high slurry temperature operation compared to low slurry temperature operation. This increase in the hardness of the CMA coating provides a product that can better withstand degradation to form dust and fines during shipping and storage.

Alternatively, the CMA slurry may be distributed onto discrete substrate particles to give a thin layer of CMA on substrate particles. Atomizing air of from about 0 to 100 psig, preferably from about 0 to about 20 psig, may be used. In a third embodiment, (if the organic chelating agent has not yet been added), the organic chelating agent (in solution or slurry) is sprayed, dripped or otherwise applied to the forming CMA layers. Preferably, said thin layer of CMA, along with the chelating agent, substantially surrounds said substrate particles and forms a substantially continuous layer. The layered substrate particles are then dried. The layered substrate particles may be recycled through the distributing and drying steps adding additional thin layers of CMA and chelating agent with each distributing and drying cycle to give a plurality of layers on said substrate particles until the desired particle size for the deicing composition is obtained.

Suitable substrate particles may be inert supports such as, for example, traction aids (sand, grained or crushed nutshells, expanded shale, etc.), or other aggregates, or preformed CMA particles. Particular preferred substrate particles include sand, especially sand of −10 to +20 mesh size, and preformed CMA particles. Preformed CMA particles may be obtained by crushing deicer compositions having layers of CMA on substrate such as that prepared by the present process and separating CMA material from inert support (if any). Preformed CMA particles may be provided by recycling a set portion of product of desired size to obtain oversized particles which are then crushed to provide a supply of preformed CMA particles.

The distributing (of CMA and organic chelating agent onto the substrate) and drying steps optionally may be carried out simultaneously, such as by distributing a thin layer of CMA slurry and organic chelating agent slurry on substrate particles in the presence of a heated gas or said distributing and drying steps may be performed separately in sequence.

In a preferred embodiment the distributing and drying steps are performed substantially simultaneously. In this embodiment, the CMA and organic chelating agent slurries are distributed onto a dense falling curtain of substrate particles in the presence of a heated gas (such as air). The heated gas contacts the substrate particles at substantially the same time as the slurry is distributed in a thin layer on the substrate particles. Droplets of slurry are distributed on the substrate particles, and the water is vaporized and removed. The flow rate and temperature of the heated gas are controlled such that the water from each forming layer of slurry on the substrate particles is quickly vaporized. Optionally, undersized substrate particles are recycled through the combined distributing and drying step to give additional layers as necessary to give the desired particle size for the substantially isodimensional product. Where preformed CMA particles comprise the substrate, product size or oversize particles may be crushed to obtain a continuous supply of preformed CMA particles or undersized particles may be used without crushing.

The layered substrate particles may be screened to remove fines which may be recycled to receive additional layers of CMA and organic chelating agent; oversized material may be fed to a suitable crusher.

The CMA-organic chelating agent deicing compositions may also be made by other methods in situ while preparing CMA from basic precursors. In general, mixtures or blends of finely divided calcium oxide (preferably as lime) and magnesium oxide may be treated with an amount of water and the effective anti-staining amount of chelating agent, the whole then reacted with glacial acetic acid. Mixtures o ores will be suitable to the process providing they provide the desired levels of chemically reactive MgO and CaO. Also, dilute acetic acid can be used, and reacted directly with the dry blend. The relative amount of water used with respect to the amounts of lime and magnesium oxide depends upon the CMA process selected. Processes for preparing CMA are disclosed, for example, in U.S. Pat. No. 4,699,725, which may be modified by adding the desired amount of chelating agent to the lime-magnesium oxide slurry.

The amount of acetic acid introduced is generally the stoichiometric equivalent of the active CaO, MgO content of the ore blend.

After reaction of the slurry with acetic acid, the viscous product solution may be poured onto a flat surface where it ultimately solidifies. The solidified material is then mechanically broken up and fed to conventional crushers.

Alternatively, raw material ore, chelating agent, water and acid streams may be simultaneously introduced to an agitated vessel containing an existing bed of solid product. The product is then optionally dried.

FIG. 1 illustrates three alternative embodiments of a process for preparing the CMA-chelating agent deicing compositions of the present invention.

In FIG. 1, water is fed through line 10, which has a suitable means for the control of rate of flow into mix tank 12. Simultaneously, CM base ("AE Base No. 1") through line 14 and, if more than one CM base is used, CM base No. 2 ("AE Base No. 2") through line 16 are fed into tank 12. If additional CM bases are used, they may be fed into tank 12 through additional feed lines. As one option, the organic chelating agent from slurry tank 15 may be added to mix tank 12 through line 17. If necessary, the organic chelating agent is mixed in tank 15 with sufficient neutralizing agent to solubilize the chelating agent at least to the extent of about 0.5% by weight in the slurry. The preferred slurry comprises EDTA and a sufficient amount of MgO and lime to neutralize two of the four acid equivalents in EDTA.

The mixture in tank 12 overflows through line 18 into optionally agitated reactor 22. Acetic acid ("carboxylic acid") is fed through line 20 into reactor 22 whereby it reacts with the CM base to give a CMA slurry. The CMA slurry overflows through line 24 into surge tank 26. Dust recovered from dust collector 66 is fed into surge tank 26 with additional water, if indicated. Heating means 28 heats the slurry in surge tank 26. Suitable heating means 28 include a steam jacket, steam coil or other heating means.

As a second option, if tank 15 is not used, the organic chelating agent may be added to tank 26 from slurry tank 25 through line 27. The chelating agent slurry is prepared as previously described.

Heated slurry is pumped from surge tank 26 through line 30 through atomizing nozzles 32 so positioned in contactor 34 so that the sprayed slurry impinges on a dense curtain of substrate particles cascading from lifters 36 in contactor 34. Substrate particles enter contactor 34 through line 38 or CMA layered substrate through recycle line 40.

As a third option, the organic chelating agent may be introduced into contactor 34 and sprayed onto the CMA-layered substrate particles. The organic chelating agent may be added to contactor 34 from tank 31 through line 33. The chelating agent slurry is prepared as previously described.

The layered substrate particles are dried in dryer 42. A stream of gas is drawn through line 44 into heating means 46 (where it is heated by natural gas or other suitable heating means) and then the heated gas is drawn through line 48 into dryer 42. In one preferred embodiment contactor and dryer means are combined so that substrate particles are dried immediately after coating. In another embodiment contactor and dryer means are separate. Layered substrate exits dryer 42 through line 50 and goes into separator means 52. Separator means 52 removes fines which are returned through line 54-40 to contactor 34 for additional coating. Oversize material goes through line 56 into crusher 58 (suitable crushers include hammermill or roll crushers) and then is returned through line 60-40 to contactor 34. The CMA salt is withdrawn through line 62 and then sent to contactor 72. (Where substrate particles comprise CMA particles, optionally a set portion of product may be recycled to contactor 34 to obtain oversized material which is then crushed to generate CMA substrate particles.) Alternately, double salt may be cooled in a rotary drum cooler or fluid bed cooler or other suitable cooling means.

Substrate particles are continuously fed through line 38 (or recycle 40) into contactor 34. Adjustments are made in the quantity of material in contactor 34 and the internal configuration of contactor 34 to minimize the return of discharge particles and to provide the most uniform level coating on each particle.

Air and dust are removed from dryer 42 through line 64. Dust is recovered in dust collector means 66. Suitable dust collector means 66 include, for example, a baghouse, wet scrubber or other conventional dust removing systems. Air is discharged to the atmosphere (outside) through line 68. Recovered dust collected in dust collector means 66 is returned through line 70 to surge tank 26. (Alternatively, where dust collector means comprise a wet scrubber, a CMA dust and water mixture may be returned to mix tank 12 through a conduit.)

Figure 2:
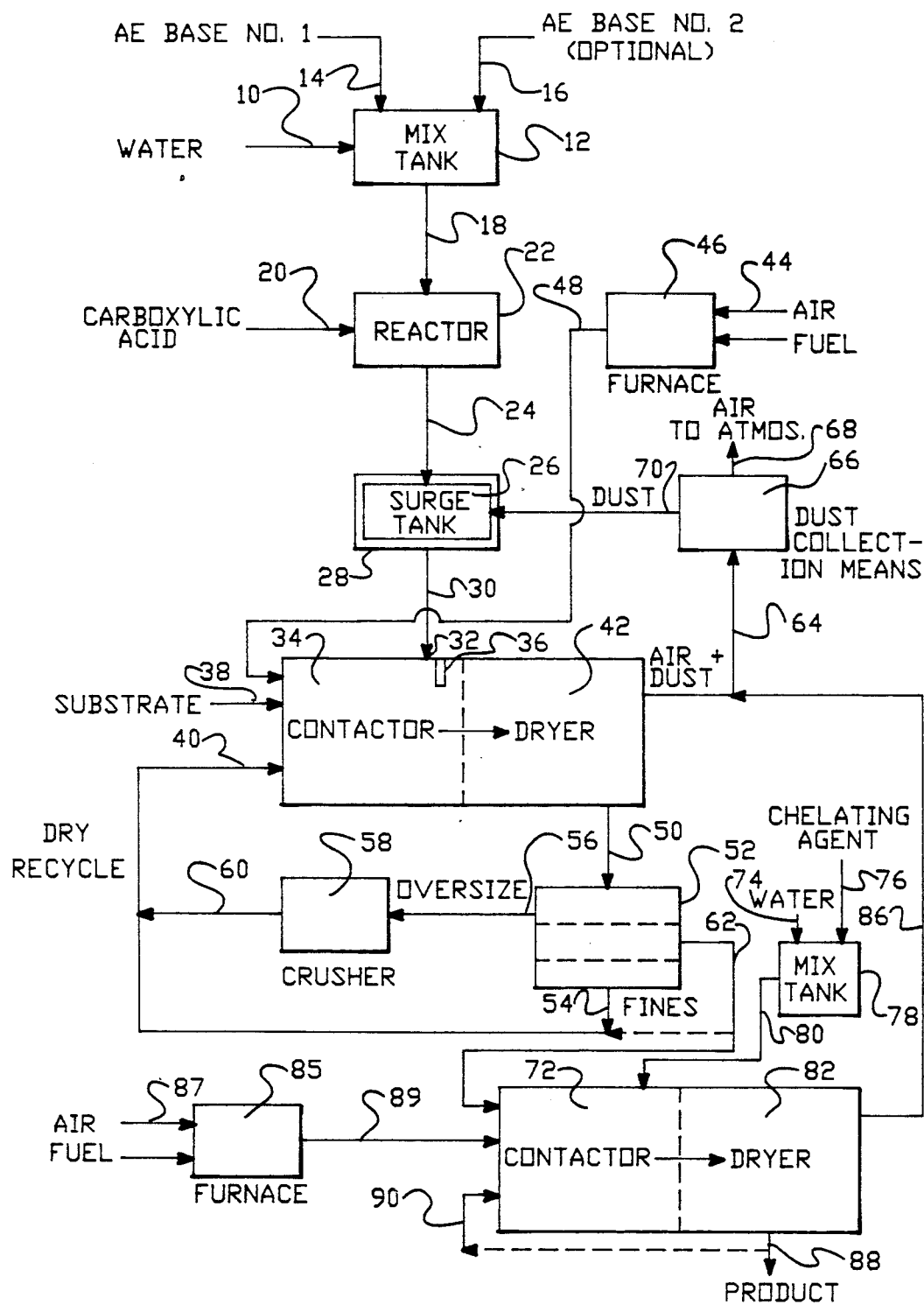
FIG. 2 is a schematic drawing showing the steps and apparatus for another process for making compositions of the present invention.

Referring to FIG. 2, there is shown a schematic drawing of the steps and apparatus for another embodiment of a process for making compositions of the present invention. As shown in the figure, reference numerals 10 through 70 are the same elements as described in connection in FIG. 1. In FIG. 2, however, the organic chelating agent slurry is added subsequent to the preparation of the CMA particles.

The CMA particles enter contactor 72 through line 62 or through recycle line 90. In this embodiment, the source of CMA particles need not necessarily be from the apparatus described in reference numerals 10 through 70. Any CMA particles from other sources and/or made by other methods may be fed into contactor 72 through an appropriate feed line (not shown). Water is fed through line 74 and chelating agent through line 76, both of which have suitable means for controlled rate of flow into mix tank 78. The chelating slurry is then mixed and introduced through line 80 into the contactor 72 preferably through atomizing nozzles (not shown) so positioned in contactor 72 so that the chelating agent slurry impinges on a dense curtain, or on a rolling bed, of CMA particles suitably agitated within contactor 72. The particles are dried in dryer 82 which is heated gas drawn through line 89. A stream of gas is drawn through line 87 into heating means 85 where it is heated by combustion of natural gas or other suitable source of heat. Air, water vapor and any extraneous dust is withdrawn through line 86 and added to the air and dust in line 64 for disposal to the atmosphere after suitable cleanup. The dried CMA-chelating agent particles are withdrawn from the dryer through line 88. If necessary to attain the proper CMA to chelating agent weight ratio, the product may be recycled through line 90 for further contact within contactor 72 with organic chelating agent slurry.

In the process for preparing the deicing compositions of our invention, either preformed or undersized CMA particles or inert support, including traction aids, may be used as substrate particles.

It will be realized that various modifications of the above-described embodiments may be made without departing from the scope of the invention. Such modifications include, but are not limited to, use of separate distributing and drying means. Suitable apparatus for separate distributing means may include drum granulators, pan granulators, pug mills and other conventional granulating and pelletizing machinery. Suitable separate drying means may include rotary drum and fluid bed dryers as well as other conventional means for drying pelleted or granulated materials. Such apparatus are used with a sufficient amount of substrate particles to give a rolling bed of substrate particles upon which the slurry may be distributed.

CONTINUOUS PREPARATION OF CMA-CHELATING AGENT COMPOSITIONS

In a preferred embodiment of the present invention, CMA-chelating agent compositions are produced by a continuous process.

Water and calcium and magnesium bases (such as calcium oxide, magnesium oxide and dolomitic lime) are continuously mixed to give an aqueous CM base mixture. Sufficient water is added to give a flowable mixture, at least about 40% by weight water. Optionally, the organic chelating agent may be continuously added at this point as previously described.

The CM base mixture and from about 70% to about 110% of the stoichiometric amount of acetic acid are simultaneously added together to give a steady state of about 1.8 mole (90% of the stoichiometric amount) acetic acid per each mole of calcium and magnesium. If too little acid is added, or the acid is added at too slow a rate, side products may form and precipitate out (for example, calcium acetate as a white precipitate and magnesium acetate as an amorphous precipitate).

Additional acetic acid is added, as needed, to maintain a slurry pH of about 7 to 9.5, preferably from about 7.5 to 8. Slurry pH is monitored; after diluting the slurry, one part slurry to four parts water, the pH of the thusly diluted slurry is measured.

The slurry is then aged for period of time sufficient to allow complete reaction. This aging may be accomplished by the slurry flowing through a series of vessels so that the combined residence times are sufficient for substantially complete reaction. Residence times on the order of about 3.5 to 4 hours are normally sufficient; longer residence times (on the order of about 10 to about 15 hours) may be used. The heat of reaction of CM base with acetic acid may give slurry temperatures above 150° F. and in the preferred range of about 170° F. and 200° F.; however, during the aging step it may be desirable to heat the slurry to maintain its temperature in the preferred range and maintain its fluidity. Optionally, the organic chelating agent may be added at this point as previously described.

After aging, the slurry is heated (if necessary) to a temperature of about at least 150° F., preferably to about 170° F. to about 200° F. The slurry is then distributed on substrate particles. The particles are then dried as described above.

If at this point the organic chelating agent has not yet been incorporated into the product, the organic chelating agent may be distributed on the dried CMA particles as described in connection with FIG. 2.

EXAMPLES

The following non-limiting examples are typical of deicing compositions prepared according to the process of the present invention. The preparations of the Examples were performed using apparatus substantially as shown in FIGS. 1 or 2.

Unless stated otherwise, measurement of slurry pH was performed after diluting the slurry one part slurry to 9 parts water and then measuring the pH of the thusly diluted slurry.

EXAMPLE 1

Preparation of Calcium Magnesium Acetate-EDTA Pellets Using Disodium EDTA

An aqueous slurry of 46 grams of acid EDTA was prepared as a 60% slurry. Dry CMA pellets prepared as described in copending Ser. No. 144,848, filed Jan. 14, 1988 (without the use of a traction aid), 833 grams, were mixed in the EDTA slurry until coated. The pellets were then transferred to a drying oven and dried overnight at about 248° F. Aluminum sandwich corrosion tests were performed on these CMA-EDTA compositions to measure staining of various aluminum coupons, following the sandwich corrosion test ASTM method F 1110-88. This composition passed the corrosion test both as prepared and when diluted, for purposes of testing only, with dry untreated CMA to give a 3% by weight EDTA-dry CMA composition.

EXAMPLE 2

CMA-EDTA Deicing Compositions Using EDTA

Aluminum sandwich corrosion tests were performed on CMA-EDTA compositions to measure staining of aluminum materials, such as those used in aircraft. The standard corrosion tests followed ASTM method F1110-88.

The test results are summarized in the attached Tables I, II and III which show comparisons of three materials made as described in Example 1 (A=CMA, B =CMA+1% EDTA, and C=CMA+3% EDTA) at each of three different concentrations in water, 5%, 15%, and 25%, respectively. Although the CMA and CMA/EDTA mixtures would not typically be used concentrations as high as 25%, drying of applied deicer could result in such concentrations. The CMA-EDTA compositions were prepared by blending dry CMA particles (prepared in accordance with Ser. No. 144,848, without the use of a traction aid) with an appropriate amount (i.e. 1% by weight or 3% by weight) of acid EDTA in an aqueous slurry in a blender. As prepared the pH of the mixture was about 5.8 when adding about 3% by weight of the EDTA. These mixtures were dried and later made to water solutions whose pHs were adjusted to simulate commercial products by adding 0.1N sodium hydroxide or 0.1N acetic acid. The Tables show test results at pH's of 9 to 10.6, which are typical pH's for these compositions in use.

As can be seen rom these Tables, at pH's between 9 and 10.6 Sample A (CMA) and Sample B (CMA with 1% EDTA) give failure in the staining test. Sample C (CMA with 3% EDTA) always passes the test. By combining the results in the three Tables (simulating evaporation and drying of the deicing composition on the aluminum), it can be seen that Sample A resulted in a total of 7 failures, Sample B resulted in a total of 5 failures and Sample C results in no failures. Moreover, Sample C gave clearly superior and generally very good results at pH's of 9.5 and higher.

TABLE I

| | Sandwich Staining Test for CMA Samples[1] Concentration = 5% | | | | | | | | | | |
|---|---|---|---|---|---|---|---|---|---|---|---|
| Sample (2) | A | | | B | | | | C | | | |
| 3.2.2 pH | 9.0 | 9.6 | 10.0 | 9.0 | 9.6 | 10.4 | 11.0 | 9.1 | 9.6 | 10.4 | 11.3 |
| QQ-A-250/4 Anodized | 2 | 2 | 2 | 2 | 2 | 2 | 2 | 2 | 2 | 1 | 2 |
| QQ-A-250/5 Clad | 2 | 2 | 2 | 3 | 2 | 2 | 2 | 1 | 1 | 1 | 1 |
| QQ-A-250/12 Anodized | 3 | 2 | 2 | 2 | 2 | 2 | 2 | 2 | 2 | 1 | 2 |
| QQ-A-250/13 Clad | 2 | 2 | 2 | 3 | 2 | 2 | 2 | 1 | 1 | 1 | 1 |

TABLE II

| | Sandwich Staining Test for CMA Samples Concentration = 15% | | | | | | | | | | |
|---|---|---|---|---|---|---|---|---|---|---|---|
| Sample (2) | A | | | B | | | | C | | | |
| 3.2.2 pH | 9.0 | 9.5 | 10.3 | 9.0 | 9.5 | 10.3 | 10.7 | 9.0 | 9.5 | 10.3 | 11.0 |
| QQ-A-250/4 Anodized | 3 | 2 | 2 | 2 | 2 | 2 | 2 | 2 | 1 | 1 | 1 |
| QQ-A-250/5 Clad | 3 | 2 | 2 | 2 | 2 | 2 | 1 | 1 | 1 | 1 | 1 |
| QQ-A-250/12 Anodized | 3 | 3 | 2 | 2 | 2 | 2 | 2 | 2 | 1 | 1 | 1 |
| QQ-A-250/13 Clad | 3 | 2 | 2 | 2 | 2 | 2 | 1 | 1 | 1 | 1 | 1 |

TABLE III

| Sample (2) | | Sandwich Staining Test for CMA Samples Concentration = 25% | | | | | | | | |
|---|---|---|---|---|---|---|---|---|---|---|
| | A | | | B | | | | C | | |
| pH | 9.2 | 9.6 | 10.4 | 9.1 | 9.7 | 10.2 | 10.6 | 9.0 | 9.5 | 10.5 | 11.0 |
| QQ-A-250/4 Anodized | 2 | 2 | 2 | 2 | 2 | 2 | 2 | 2 | 1 | 1 | 1 |
| QQ-A-250/5 Clad | 2 | 3 | 2 | 2 | 3 | 3 | 2 | 2 | 1 | 2 | 1 |
| QQ-A-250/12 Anodized | 2 | 2 | 1 | 3 | 2 | 2 | 2 | 1 | 1 | 1 | 1 |
| QQ-A-250/13 Clad | 2 | 2 | 2 | 2 | 2 | 2 | 2 | 2 | 2 | 1 | 1 |

(2) Sample A = CMA
Sample B = CMA + 1% EDTA
Sample C = CMA + 3% EDTA
(1) Test Scale
0 = No visible corrosion/PASS
1 = Very slight corrosion or discoloration/PASS
2 = Slight corrosion/PASS
3 = Moderate corrosion/FAIL
4 = Extensive corrosion, pitting/FAIL

EXAMPLE 3

Preparation of CMA-EDTA Deicing Compositions Using Neutralized EDTA

To simulate a commercial preparation, to an aqueous slurry of 30 grams of acid EDTA in 1.5 liters, a basic slurry of 40 g. type S high magnesium dolomitic lime (Chemstar), 18.4 g. Mag-Plus grade 20 magnesium oxide (National Magnesia) and 225 g. water was added until pH 8 was obtained. To this slurry was added 970 grams of CMA solids (prepared in accordance with copending Ser. No. 144,848, without the use of a traction aid). This slurry was dried in a microwave oven to give a CMA-EDTA solid which was less than 10% water. The CMA-EDTA solids were then added at 1 part to 14 parts water for the following tests in accordance with standard SMA 1426A. The results are shown below in Table IV. Some of the qualifications do not apply to CMA since AMS 1426A was designed to qualify only glycol (and glycol mixtures), whereas AMS 1730A applies to urea. The performance requirements, i.e., the corrosion tests, are essentially the same in both cases.

TABLE IV

Qualification of CMA-EDTA Powder Under AMS 1426A for Deicing/Anti-icing Fluid For Use on Runways and Taxiways

| 3.1 | Technical Requirements: |
|---|---|
| 3.1 | Material: The composition of the fluid shall be optional with the manufacturer but shall contain glycol, urea, formamide and corrosion inhibitors as required to produce a product meeting the requirements of 3.2 Result Does not apply |
| 3.2 | Properties: The fluid shall conform to the following requirements; tests shall be performed in accordance with specified test methods on the product supplied in concentrated form: |
| 3.2.1 | Specific Gravity: Shall be within +0.005 of the qualification value established as in 4.4.1, determined in accordance with ASTM D 891. Result (Powder sample) Does not apply |
| 3.2.2 | pH: Shall be within +0.5 of the qualification value established as in 4.4.1, determined in accordance with ASTM E70. 8.4 pH (1:5 solution) Result Qualification value |
| 3.2.3 | Flash Point: Shall not be lower than 100° C. (212° F.), determined in accordance with ASTM D56 or ASTM D3278. In case of conflict, flash point determined in accordance with ASTM D 56 shall apply. Result Conform no flash |
| 3.2.4 | Eutectic Point (Slush or Freeze Point): Shall be not higher than −23° C. (−10° F.), determined in accordance with ASTM D1177. Result (Powder sample) Does not apply |
| 3.2.5 | Corrosion of Metal Surfaces: |
| 3.2.5.1 | Sandwich Corrosion: Specimens of AMS 4037 and AMS 4049 aluminum alloy, after test, shall show a rating not worse than 2, determined in accordance with ARP 1512. 4037 Pass 4049 Pass Result Conform |
| 3.2.5.2 | Total Immersion Corrosion: The fluid shall neither show evidence of corrosion nor cause a weight change of any single test panel greater than the following, determined in accordance with ASTM F 483: |

| Test Panel | Weight change mg/cm²/24 hr | Result |
|---|---|---|
| AMS 4037 or QQ-A-250/4 Al alloy anodized as in AMS 2470 | 0.3 | −.14 |
| AMS 4041 or QQ-A-250/5 Al alloy (optional) | 0.3 | −.12 |
| AMS 4049 or QQ-A-250/13 Al alloy | 0.3 | −.10 |
| AMS 4376 or QQ-M-44, alloy AZ31B, Mg alloy dichromate treated as in AMS 2475 | 0.2 | −.13 |
| AMS 4911 or Mil-T-9046, Type III Composition C, Titanium alloy | 0.1 | −.09 |
| ASTM A109, Temper No. 1 or QQ-S-698,, condition 1, Steel | 0.8 | −.11 |
| Result Conform | | |

| 3.2.5.3 | Low-Embrittling Cadmium Plate: Test panels coated with low-embrittling Cadmium plate shall not show a weight change greater than 0.3 (mg/cm²) 24 hr, determined in accordance with ARP 1511. .15 mg/cm²/24 hr Result Conform |
|---|---|
| 3.2.6 | Hydrogen Embrittlement: The fluid shall be non-embrittling, determined in accordance with ASTM F-519, Method 2a. Result Conform |
| 3.2.7 | Effect on Transparent Plastics: The fluid shall not craze, stain, or discolor Type C acrylic plastic, determined in accordance with ASTM F 484. The fluid shall not craze, stain or discolor Mil-P-83310 polycarbonate plastic or polysulfone plastic, determined in accordance with test procedures specified in ASTM F 484 on specimens stressed for 30 minutes ± 2 to an outer fiber stress of 3000 psi (20 MPa). Result Conform |

TABLE IV-continued

| | |
|---|---|
| 3.2.8 | Effect on Painted Surfaces: The fluid shall neither decrease the paint film hardness by more than two pencil hardness levels nor shall it produce any streaking, discoloration, or blistering of the paint film, determined in accordance with ASTM F502.<br>Result Conform |
| 3.2.9 | Effect on Unpainted Surfaces: The fluid, tested in accordance with AST F485, shall neither produce streaking nor leave any stains requiring polishing to remove.<br>Result Conform |
| 3.2.10 | Rinsibility: The fluid shall be completely rinsible in tap water, determined in accordance with 3.2.10.1. |
| 3.2.10.1 | A 75 × 200 (3 × 8 in.) panel of clear glass shall be cleaned to provide a surface free of waterbreak, dried, and coated with the deicer/anti-icer fluid by pouring the fluid over the panel while it is held in a horizontal position. The coated panel shall be inclined at approximately 45° for 10 min. ± 0.5, then placed in a horizontal position for 24 hr ± 0.25 at room temperature. After the 24 hr exposure, the panel shall be rinsed in tap water for 5-6 min., rinsed in distilled or deionized water, dried, and examined for visible traces of the deicer/anti-icer fluid.<br>Result Conform |
| 3.2.11 | Pavement Compatibility: |
| 3.2.11.1 | Scaling Resistance: The condition of the surface shall have a rating not greater than 2, determined in accordance with ASTM C672 except that a 25% by volume solution of the deicer/anti-icer fluid in tap water shall be substituted for calcium chloride.<br>Product tested as a 25% slurry<br>Result Conform Rating of 1 |
| 3.2.11.2 | Slipperiness: Friction limits shall be as follows, determined on concrete and asphalt surfaces, both wet and dry, using a Mu meter and with a deicer/anti-icer fluid thickness of 1 mm (0.04 in.) using a NASA depth gauge. A basis reading shall be determined on wet and dry concrete and wet and dry asphalt before application of the deicer/anti-icer fluid.<br>Test dry and wet. Using a portable slipperiness tester NBS. All readings above .25 coefficient of friction.<br>Result Conform/Not considered slippery. |

These results demonstrate that CMA-EDTA surprisingly meets all the relevant criteria for the standard test for deicing compositions used for airport runways and taxiways.

EXAMPLE 4

Continuous Production of CMA-EDTA

A CMA-EDTA deicer is produced on a commercial scale by the following continuous process.

Water is continuously added to an agitated mixing vessel (at a rate sufficient to maintain about 42 weight percent CMA-EDTA slurry) on exiting the reactor train with approximately 2120 pounds/hour of Type S hydrated dolomitic lime and approximately 990 pounds/hour of magnesium oxide. The resulting mixture is flowed by gravity through an additional mixing vessel, overflowing one through a trough into the next.

Upon overflowing the second mixing vessel, glacial acetic acid is added at a rate of approximately 10.9 gallons/minute and EDTA is added at a rate of approximately 3.8 pound/minute to a reactor with thorough mixing, resulting in an exit pH of approximately 9. As the slurry overflows into the second reactor, a slight flow of additional acetic acid is added to maintain a slurry pH of approximately 7.5 in the slurry tank. The reactors are vented through a high-energy wet scrubber to reduce acetic acid emissions to the environment. The water from this scrubber is continuously used as feed water to the first mixing vessel.

The overall formula for the CMA slurry is:

| | |
|---|---|
| Acetic Acid | 0.765 pounds/pound dried CMA |
| EDTA | 0.03 pounds/pound dried CMA |
| Type S Lime | 0.26 pounds/pound dried CMA |
| Magnesium Oxide | 0.12 pounds/pound dried CMA |

The resultant slurry is maintained at a temperature of approximately 190° F. (88° C.) and is pumped through a nozzle and is sprayed on a falling bed of CMA pellets in the front of a rolling drum. The drum is equipped with internal lifters, an internal dam and an external solids recycle system. Also included is an air system consisting of a fan, an inlet air heater and a baghouse dust collector on the outlet air. Air is introduced at a temperature of approximately 800° F. (427° C.), and a flow rate of approximately 32,000 standard cubic feet per minute (SCFM). The air exits the drum at approximately 200° F. (93° C.) and enters a baghouse for dust removal before entering the environment. The dust is collected from the baghouse, and approximately 500 pounds/hour is recycled to the slurry tank and additional water is added to maintain approximately a 58 weight percent moisture slurry.

Upon exiting the drum, CMA-EDTA pellets formed or enlarged in the drum are classified with a screening system. Pellets which are larger than a 6-mesh screen are crushed and recycled to the front of the drum. Pellets which are smaller than an 8-mesh screen are also recycled. Approximately 5 percent of the pellets from the drum are in the product range of minus 6-mesh to plus 8-mesh and are withdrawn as product and moved to the warehouse. The remaining 95 percent is recycled to the front of the drum.

Product produced from this run has a calcium/magnesium mole ratio of approximately 0.46 (about 1 to 2.2), has a pH of about 9.5, and constitutes about 2 weight percent water insoluble material.

EXAMPLE 5

Production of Sodium Formate-EDTA

Sodium formate product which contains a chelating agent as an added protection against aluminum staining in airport use is prepared from a warm solution of about 50 percent sodium formate in water either by dissolving sodium formate into the water, or by direct use of a process solution from which sodium formate is produced by the reaction of sodium hydroxide and carbon monoxide or as a by-product from some other manufacturing process. To this sodium formate solution is added an amount of EDTA which is equivalent to about 0.5 to 3 percent of the weight of the solids present in the solution. The EDTA is added either as the tetra-sodium salt or in its acid form depending on the pH of the solution and on the relative costs of the additives. In either case, the pH of the EDTA-additized solution is adjusted to about 8 before the solution is dried or used directly in its liquid form.

What is claimed is:

1. An anti-staining deicing composition consisting essentially of a major amount of calcium magnesium acetate and a minor amount of alkaline earth and/or alkali metal base, common impurities in said bases, and at least 3% by weight of ethylenediamine tetraacetic acid in any of its acid or neutralized forms.

2. A composition according to claim 1 wherein said calcium magnesium acetate is of the formula

wherein x is about 2-6 and y is about 8-4.

3. A composition according to claim 2 wherein x is 3 or 4 and y is 7 or 6.

4. A composition according to claim 1 wherein said ethylenediamine tetraacetic acid is characterized by a solubility in water in its neutralized form of at least about 0.3% by weight.

5. A composition according to claim 1 wherein said bases and impurities comprise less than about 3% by weight magnesium base and less than about 5% by weight water.

6. A composition according to claim 1 which is substantially anhydrous.

7. A composition according to claim 3 having a calcium:magnesium ratio of about 4:6 to about 3:7.

8. A composition according to claim 3 having a calcium:magnesium ratio of about 3:6 to about 3:7.

9. A non-staining deicing composition which comprises a plurality of layers of a composition according to claim 1 on discrete substrate particles.

10. The method of melting snow and/or ice accumulated or formed on a surface for vehicular use comprising the step of contacting said surface with an effective deicing amount of a composition according to any one of claims 1, 2 to 5, and 6 to 7.

11. A method according to claim 10 wherein said surface comprises an airport runway or taxiway.

12. A method of preventing accumulation of ice on a surface for vehicular use comprising the step of contacting said surface with an effective ice preventing amount of a composition according to any one of claims 1, 2 to 5, and 6 to 9.

13. A method according to claim 12 wherein said surface comprises an airport runway or taxiway.

* * * * *

UNITED STATES PATENT AND TRADEMARK OFFICE
CERTIFICATE OF CORRECTION

PATENT NO. : 5,132,035
DATED : July 21, 1992
INVENTOR(S) : Karl A. Hoenke, et al It is certified that error appears in the above-indentified patent and that said Letters Patent is hereby corrected as shown below:

On the title page, insert the following: --[63] Continuation of Ser. No. 319,447, filed Mar. 6, 1989, abandoned.--.
Column 1, line 5, insert the following: --This application is a continuation of application Ser. No. 319,447, filed Mar. 6, 1989, abandoned.--.

In Column 1, Line 11: "19888" should read -- 1988 --

In Column 9, Line 64: "o" should read -- of --

In Column 14, Line 25: "rom" should read -- from --

In Column 15, Line 37: "SMA" should read -- AMS --

Signed and Sealed this

Twenty-fifth Day of January, 1994

Attest:

BRUCE LEHMAN

Attesting Officer          Commissioner of Patents and Trademarks